(12) United States Patent
Tschuncky

(10) Patent No.: US 6,685,808 B2
(45) Date of Patent: Feb. 3, 2004

(54) ELECTROCHEMICAL GAS SENSOR WITH FOLDED MEMBRANE STRIP

(75) Inventor: Peter Tschuncky, Lübeck (DE)

(73) Assignee: Dragerwerk Aktiengesellschaft, Lübeck (DE)

(*) Notice: Subject to any disclaimer, the term of this patent is extended or adjusted under 35 U.S.C. 154(b) by 0 days.

(21) Appl. No.: 10/288,321

(22) Filed: Nov. 5, 2002

(65) Prior Publication Data
US 2003/0150725 A1 Aug. 14, 2003

(30) Foreign Application Priority Data
Feb. 12, 2002 (DE) ............................ 102 05 675

(51) Int. Cl.[7] ............................ G01N 27/404
(52) U.S. Cl. ................ 204/415; 204/286.1; 204/295; 204/296; 204/297.01
(58) Field of Search ............... 204/415, 286.1, 204/295, 296, 297.01; 205/782.5, 783

(56) References Cited

U.S. PATENT DOCUMENTS 4,329,214 A * 5/1982 Spritzer et al.
5,108,564 A * 4/1992 Szuminsky et al.

FOREIGN PATENT DOCUMENTS

| DE | 198 45 318 | 4/2000 |
| WO | WO 98/25138 | 6/1998 |

* cited by examiner

Primary Examiner—T. Tung
(74) Attorney, Agent, or Firm—McGlew and Tuttle, P.C.

(57) ABSTRACT

An electrochemical gas sensor is provided which can be assembled economically and in a few steps. The electrodes (1, 2, 3) with associated electric lines are applied in a planiform manner to a membrane strip, which is impermeable to the electrolyte but permeable to gases. The membrane strip (6) is deposited in the sensor housing in a zigzag-folded pattern, so that the membrane strip limits the opening of the sensor housing for the entry of the measured gas. The electrodes (1, 2, 3) are arranged stacked in the sensor housing (5, 7) at spaced locations from one another due to the membrane strip (6) deposited in a zigzag-folded pattern.

20 Claims, 2 Drawing Sheets

ELECTROCHEMICAL GAS SENSOR WITH FOLDED MEMBRANE STRIP

FIELD OF THE INVENTION

The present invention pertains to an electrochemical gas sensor with at least two electrodes and an electrolyte in a sensor housing with an opening for the entry of the measured gas and also relates to a method of forming an electrochemical gas sensor.

BACKGROUND OF THE INVENTION

An electrochemical gas sensor of this class is shown, e.g., in DE 198 45 318 C2. In all such prior-art gas sensors, the electrodes used are introduced into a sensor housing separately and individually, and are contacted by means of suitable wires or pins, and the electric contacts are led out through the sensor housing. The electrodes are arranged stacked at spaced locations from one another. Separators in the form of, e.g., porous, electrolyte-impregnated glass mats are used for this purpose, so that no electric short-circuit can develop between the electrodes. These prior-art electrochemical gas sensors require a great, predominantly manual effort for their assembly, which is, moreover, complicated and may lead to errors.

WO 98/25 138 shows the stacked design of a plurality of fuel cells. Each individual fuel cell has separate supply lines for two different gases, which are located above and below the optionally folded electrode array limited by gas-permeable membranes.

SUMMARY OF THE INVENTION

The object of the present invention is to provide a simple electrochemical gas sensor that can be assembled in a few steps.

According to the invention, an electrochemical gas sensor is provided with at least two electrodes and an electrolyte in a sensor housing with an opening for the entry of the measured gas. The electrodes with the associated electric lines are applied in a planiform manner on a gas-permeable membrane strip that is impermeable to the electrolyte. The membrane strip is deposited in the sensor housing in a zigzag-folded pattern, so that the membrane strip limits the opening of the sensor housing for the entry of the measured gas. The electrodes are arranged stacked at spaced locations from one another in the sensor housing due to the membrane strip deposited in a zigzag-folded pattern.

An essential advantage of the present invention arises especially from the fact that the membrane strip, which accommodates the electrodes and their electric lines and is impermeable to the electrolyte and permeable to gases, is manufactured in an automated manner at low cost, so that the complicated and time-consuming assembly of the individual components, which has hitherto been usual, is eliminated. The electrodes and their electric lines are preferably printed or sintered, sputtered or vapor-deposited on the membrane strip continuously in an operation preceding the assembly of the sensor housing. The membrane strip is subsequently separated section by section, so that each membrane strip section has the electrodes and electric lines intended for one gas sensor.

The electrodes with their associated electric lines are applied in a planiform manner on the membrane strip at spaced locations on one side in the longitudinal direction of the membrane strip and optionally additionally in a laterally offset pattern such that the membrane strip, deposited in the sensor housing folded in a zigzag pattern, brings about the electrical separation of the electrodes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
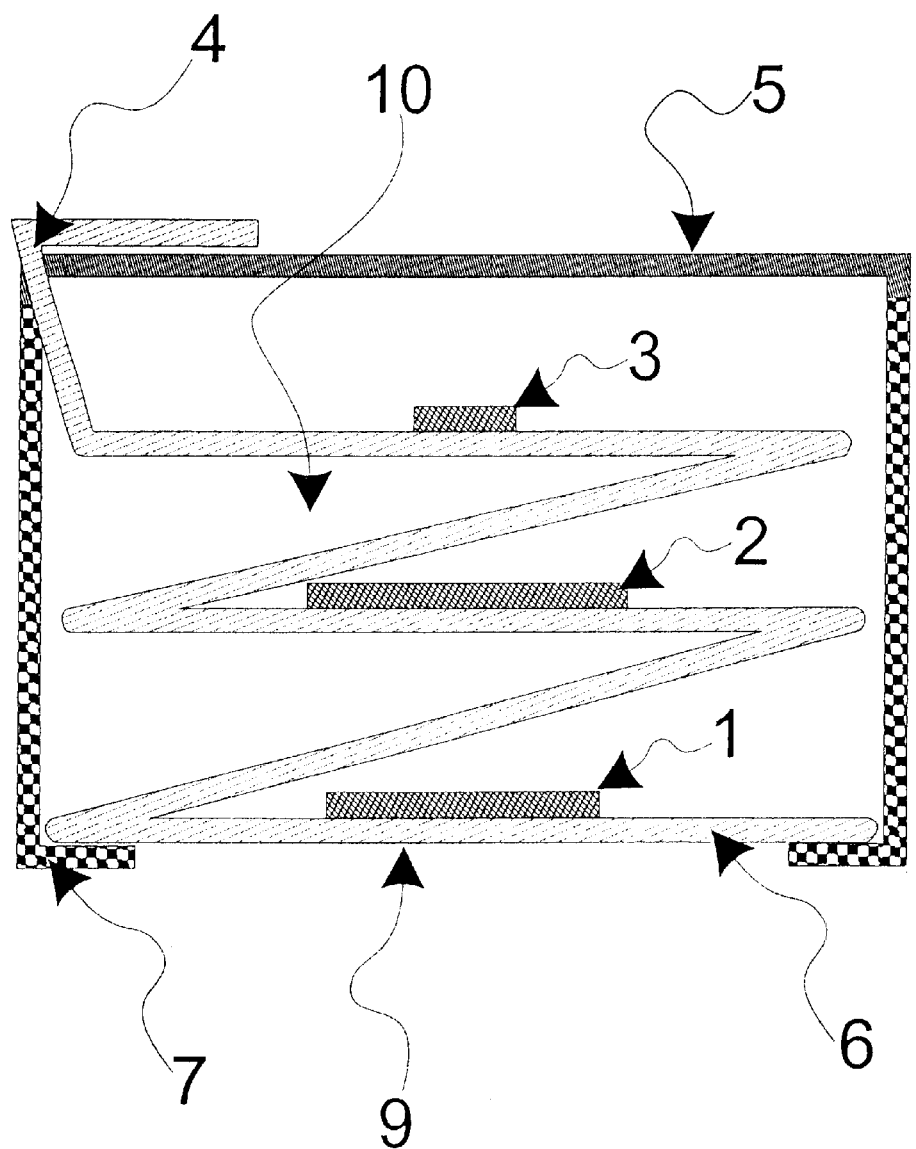
FIG. 1 is a sectional view through an electrochemical gas sensor shown schematically.
Figure 2:
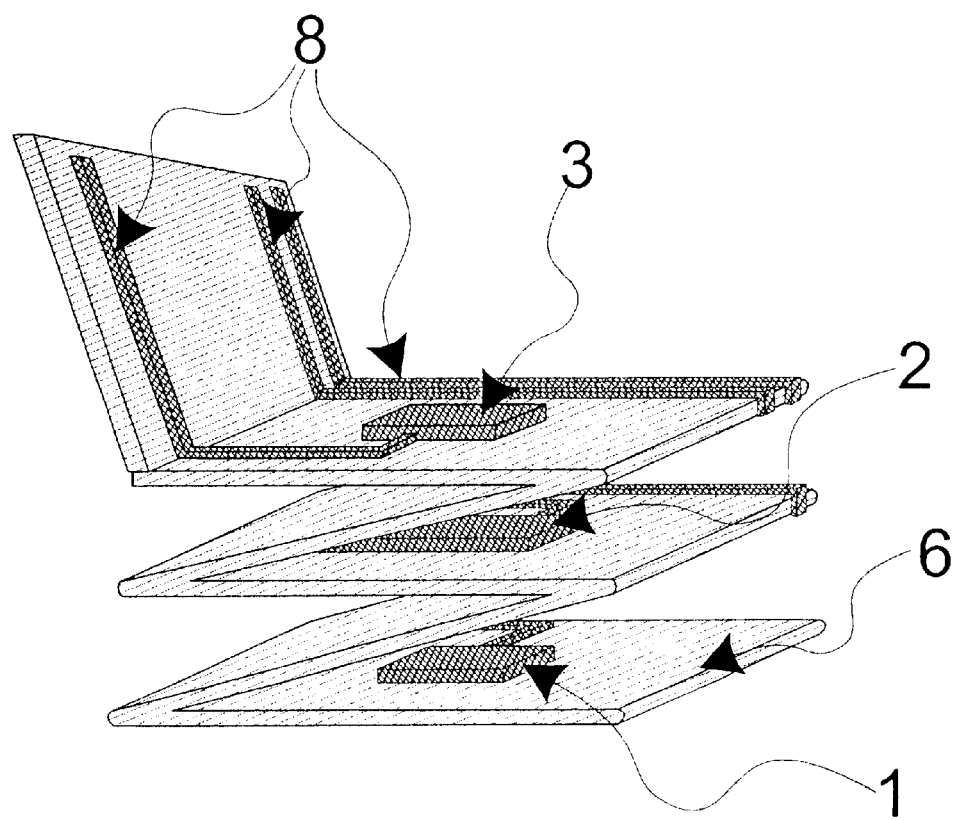
FIG. 2 is a three-dimensional view of the membrane strip of the gas sensor according to FIG. 1, which membrane strip is folded in a zigzag pattern.

Referring to the drawings in particular, the electrochemical gas sensor in FIG. 1 has an outer, two-part sensor housing 5, 7, which consists of a gas-impermeable material, especially a plastic such as polypropylene, PMMA (polymethyl methacrylate), PSU (polysulfone), polyethylene, or PTFE (polytetrafluoroethylene).

The sensor housing 5, 7 has an opening 9. In the exemplary embodiment, the sensor housing 5, 7 comprises two assembled housing parts, namely, a first housing part 7, which is the lower housing part in FIG. 1, and a second housing part 5, which is the upper housing part in FIG. 1.

A gas-permeable, but liquid-impermeable membrane strip 6, which is folded in a zigzag pattern, with electrodes 1, 2, 3 and associated electric lines 8, is bonded or welded in the first housing part 7 such that the opening 9 is covered and closed from the inside, as a result of which the gas sensor can be used in a liquid medium or in a gaseous environment for measuring the concentration of the gas to be measured, i.e., the measured gas.

The measured gas, which may also consist of a plurality of components, diffuses through the membrane strip 6 into the sensor housing 5, 7 in the area of the opening 9 in a controlled manner, and the measurement at the electrodes 1, 2, 3 printed or sputtered on the membrane strip 6 leads to the determination of the concentration of the measured gas via electrochemical reactions, which are known per se, and whose signals are evaluated separately outside the sensor housing 5, 7.

The electric lines 8 are printed on the membrane strip 6 in the longitudinal direction, preferably as strip conductors with an insulating layer, so that they are led out through a passageway 4 of the sensor housing 5, 7 with the membrane strip 6, and the measured signals are sent via contacts to a prior-art evaluating unit, not shown, for evaluation. The passageway 4 is also used for the pressure equalization with the environment during the use of the gas sensor. The membrane strip 6 is connected to the electrodes 1, 2, 3 and the associated electric lines 8, e.g., to a measuring electrode 1, a counterelectrode 2 and a reference electrode 3, being connected in the longitudinal direction of the membrane strip 6 at such a distance that a direct electric contact with the consequence of a short-circuit between two electrodes 1, 2, 3 each and the electric lines 8 provided with an insulating layer is prevented from occurring or ruled out by the membrane strip 6 deposited in the sensor housing 5, 7 in a zigzag-folded pattern.

A second measuring electrode for simultaneously measuring a second measured gas can be provided.

The membrane strip 6 consists of a gas-permeable, especially porous PTFE (polytetrafluoroethylene) material, as is available commercially, e.g., under the names Zitex, Nucleopore or Gore membrane.

As a result, the present invention provides an inexpensive electrochemical gas sensor, which can be manufactured in a simple manner and unites all the known and necessary sensor elements on the membrane strip 6 deposited in the sensor housing 5, 7 in a zigzag-folded pattern. The electrodes 1, 2, 3 and electric lines 8 are printed on the membrane strip 6 itself in a preceding, extensively automated production process, separated section by section, and subsequently bonded or welded into the first housing part 7. Before the housing parts of the sensor housing 5, 7 are connected to one another, the interior space is filled with an electrolyte, and the membrane strip 6 is led out with the electric lines 8 through the passageway 4. Compared with the prior-art stacked electrochemical gas sensors, gas sensors according to the present invention can be manufactured in a substantially simpler manner.

The connected sensor housing 5, 7 has an electrolyte space 10, which is filled with the measured gas-specific electrolyte. For better wetting and better action of the electrolyte, a mat strip, likewise folded in a zigzag pattern, may be arranged on the membrane strip 6. The mat strip preferably consists of glass fibers or another, especially porous, chemically inert material absorbing electrolyte.

The electrodes consist, in general, of a precious metal, such as gold, platinum, iridium, silver or an electrically conductive carbon material, such as graphite, doped diamond or a sintered material containing one or more of the components.

The membrane strip 6 has a thickness of 10 $\mu$m to 1 mm, preferably 200 $\mu$m to 300 $\mu$m. In the exemplary embodiment, the membrane strip 6 has a thickness of about 250 $\mu$m.

While specific embodiments of the invention have been shown and described in detail to illustrate the application of the principles of the invention, it will be understood that the invention may be embodied otherwise without departing from such principles.

What is claimed is:

1. An electrochemical gas sensor comprising:
    a sensor housing
    at least two electrodes in said sensor housing;
    an electrolyte in said sensor housing, said housing having an opening for the entry of the measured gas;
    a gas-permeable membrane strip that is impermeable to the electrolyte, said gas-permeable membrane strip having electric lines, said electrodes being applied to said gas-permeable membrane strip in a planiform manner, said membrane strip being deposited in said sensor housing in a zigzag-folded pattern with the membrane strip limiting said opening of the sensor housing for the entry of the measured gas and said electrodes are arranged stacked at spaced locations from one another based on the zigzag-folded pattern of the gas-permeable membrane strip.

2. An electrochemical gas sensor in accordance with claim 1, wherein said membrane strip is provided with a mat material that accommodates electrolyte and is arranged in folds of said membrane strip.

3. An electrochemical gas sensor in accordance with claim 1, wherein said membrane strip consists of a porous material.

4. An electrochemical gas sensor in accordance with claim 3, wherein said membrane strip consists of porous PTFE (polytetrafluoroethylene).

5. An electrochemical gas sensor in accordance with claim 1, wherein said at least two electrodes include a first measuring electrode for the measurement of a first measured gas, a second measuring electrode for the simultaneous measurement of a second measured gas and at least one additional electrode used as counter electrode.

6. An electrochemical gas sensor in accordance with claim 1, wherein the sensor housing consists of an electrically insulating material.

7. An electrochemical gas sensor in accordance with claim 6, wherein the sensor housing consists of one or more of polypropylene, polyethylene, PMMA (polymethyl methacrylate), PSU (polysulfone) and PTFE (polytetrafluoroethylene).

8. An electrochemical gas sensor in accordance with claim 1, wherein the sensor housing has a passageway for leading the membrane strip with the lines of the electrodes.

9. An electrochemical gas sensor in accordance with claim 1, wherein the membrane strip has a thickness of 10 $\mu$m to 1 mm.

10. An electrochemical gas sensor in accordance with claim 1, wherein the membrane strip has a thickness of 200 $\mu$m to 300 $\mu$m.

11. An electrochemical gas sensor comprising:
    a first electrode;
    a second electrode
    a sensor housing;
    an electrolyte in said sensor housing, said housing having an opening for the entry of a gas to be measured;
    a gas-permeable membrane strip disposed in the sensor housing with at least one fold, providing at least a first portion on one side of said fold and a second portion on another side of said fold, said first electrode being connected to said gas-permeable membrane strip first portion and said second electrode being connected to said gas-permeable membrane strip second portion.

12. An electrochemical gas sensor according to claim 11, wherein a position of said first electrode relative to said fold and a position of said second electrode relative to said fold defines a stacked arrangement of said first electrode and said second electrode in the sensor housing at spaced locations from one another.

13. An electrochemical gas sensor according to claim 11, wherein said membrane strip is impermeable to the electrolyte and said membrane strip is disposed in said sensor housing in a zigzag-folded pattern with the membrane strip limiting said opening of the sensor housing for the entry of the measured gas through said opening.

14. An electrochemical gas sensor according to claim 11, wherein said membrane strip has electric lines with each of said lines connected to a respective one of said first electrode and said second electrode with said electrodes on a common side of said membrane strip.

15. An electrochemical gas sensor formed by the steps of:
    providing a gas-permeable membrane strip that is impermeable to an electrolyte;
    providing electric lines on the membrane strip;
    applying electrodes to the gas-permeable membrane strip in a planiform manner;
    folding the membrane strip in a zigzag-folded pattern with adjacent electrodes on the membrane strip separated by at least one zigzag fold;

depositing the membrane strip in a sensor housing; and filling the sensor housing with the electrolyte.

16. An electrochemical gas sensor according to claim 15, wherein said housing has an opening and said membrane strip is disposed in the housing limiting said opening for the entry of a measured gas through said opening.

17. An electrochemical gas sensor according to claim 15, wherein said membrane strip is formed by separating from a larger membrane strip.

18. An electrochemical gas sensor in accordance with claim 17, wherein said membrane strip is provided with a mat material that accommodates electrolyte and is arranged in folds of said membrane strip.

19. An electrochemical gas sensor in accordance with claim 17, wherein said membrane strip consists of a porous material.

20. An electrochemical gas sensor in accordance with claim 17, wherein said membrane strip consists of porous PTFE (polytetrafluoroethylene).

* * * * *